United States Patent [19]

Nakamura et al.

[11] Patent Number: 5,342,831
[45] Date of Patent: Aug. 30, 1994

[54] EPITHELIOCYTE GROWTH ACCELERATOR

[75] Inventors: Toshikazu Nakamura, 11-6, Midorigaoka 3-chome, Higashi-ku, Fukuoka-shi, Fukuoka 813; Kunio Matsumoto, 11-5-308, Hakozaki 5-chome, Higashi-ku, Fukuoka-shi, Fukuoka 812, both of Japan

[73] Assignees: Toyo Boseki Kabushiki Kaisha, Osaka; Toshikazu Nakamura, Osaka, both of Japan

[21] Appl. No.: 815,333

[22] Filed: Dec. 27, 1991

[30] Foreign Application Priority Data

Dec. 28, 1990 [JP] Japan .................. 2-419158

[51] Int. Cl.$^5$ .............. C07K 13/00; A61K 37/02; A61K 37/66
[52] U.S. Cl. .................. 514/12; 530/399; 435/240.1
[58] Field of Search ........... 530/399, 350; 514/12; 435/240.1

[56] References Cited

U.S. PATENT DOCUMENTS 5,004,805  4/1991  Gohda et al. .................. 530/399

FOREIGN PATENT DOCUMENTS

0412557A1  9/1990  European Pat. Off. .
WO90/10651  9/1990  PCT Int'l Appl. .
WO91/12272  8/1991  PCT Int'l Appl. .

OTHER PUBLICATIONS

Nakamura et al. "Molecular Cloning and Expression of Human Hepatocyte Growth Factor" Nature 342 440-443, Nov. 23, 1989.
Rubin et al. "A broad-spectrum human lung fibroblast-derived mitogen..." Proc. Natl. Acad. Sci. USA 88 415-419 Jan. '91.
Gherardi et al., "Purification of scatter factor, a fibroblast-derived basic protein that modulates epithelial interactions and movement," *Proc. Natl. Acad. Sci. USA*, 86, 5844–5848 (1989).
Kan et al., "Hepatocyte Growth Factor/Hepatopoietin A Stimulates the Growth of Rate Kidney Proximal Tubule Epithelial Cells (RPTE), Rat Nonparenchymal Liver Cells, Human Melanoma Cells, Mouse Keratinocytes and Stimulates Anchorage-Independent Growth of SV-40 Transformed RPTE," *Biochem. and Biophys. Res. Comm.*, 174(1), 331-337 (1991).
Zarnegar et al., "NH$_2$-Terminal Amino Acid Sequence of Rabbit Hepatopoietin A, A Heparin-Binding Polypeptide Growth Factor for Hepatocytes," *Biochem. and Biophys. Res. Comm.*, 163(3), 1370-1376 (1989).

*Primary Examiner*—Robert J. Hill, Jr.
*Assistant Examiner*—Shelly Guest Cermak
*Attorney, Agent, or Firm*—Leydig, Voit & Mayer, Ltd.

[57] ABSTRACT

An epitheliocyte growth accelerator containing a hepatocyte growth factor (HGF) as the active ingredient. In the present invention, the HGF maybe derived from human tissues, animal tissues, or blood components, or it may be produced genetic engineering. In this regard, the host cell to be used in the genetic engineering may be selected from among *Escherichia coli, Bacillus subtilis*, yeasts, filamentous fungi, plant cells and animal cells. The epitheliocyte growth accelerator of the present invention specifically accelerates growth of normal epitheliocytes, and improves cell motility.

The epitheliocyte growth accelerate of the present invention does not have fibroblast growing activity or canceration accelerating activity.

8 Claims, 5 Drawing Sheets

EPITHELIOCYTE GROWTH ACCELERATOR

FIELD OF THE INVENTION

The present invention relates to an epitheliocyte growth accelerator containing a hepatocyte growth factor as the active ingredient.

BACKGROUND OF THE INVENTION

The skin consists of epidermis, dermis and hypodermis, of which the epidermis is what is called epithelium and derives from ectoderm, while the dermis and the hypodermis are connective tissues deriving from mesoderm (mesenchyma). The epidermis is stratified by germinative layer (basal layer), prickle-cell layer, granular layer, and so on. The cells which constitute epidermis are roughly divided into epidermal cells called malpighian cells or keratinocytes, and melanocytes having branch-like projections. The keratinocyte is characterized by keratinization and the melanocyte is characterized by melanin production. The keratinocytes are main cells constituting the entire epidermis, and the melanocytes exist mainly in the germinative layer of the epidermis.

The outermost part of the epidermis is called corneous layer and is a sediment of scale-shaped dead cells, which contains keratin in a large amount. The regeneration of epitheliocytes involves the steps of keratinocyte regeneration in the innermost germinative layer, moving thereof to the upper end of the corneous layer, and scaling off, which undergo in about 15 to 30 days' cycles.

While melanocytes produce melanin, pigment amount does not depend on the number of the melanocytes, but on pigment production and pigment distribution of the melanocytes. For example, there is no difference in distribution density of melanocytes between races such as blacks and whites, but if the produced melanin granules gather at one place, the color of the skin becomes fair, and if small granules widely spread, if becomes dark.

Both morphologically and functionally, the epidermis can be considered a symbiotic tissue of two independent cell elements —keratinocyte and melanocyte.

As the growth factor for epitheliocytes, EGF (epidermal growth factor) has been under investigations in terms of clinical effects [Nanney, L. B., J. Invest, Dermatol., 95, 624–629 (1990)], and large scale production (Earth Chemical Company, Japanese Patent Unexamined Publication No. 104293/1990), aiming at its practical use. EGF is a polypeptide consisting of 53 amino acids, which has a molecular weight of about 6 kD (kilodalton) and is known to have a cell growth accelerating effect on epitheliocytes, fibroblasts and vascular endothelial cells.

Although various effects have been expected of EGF as a medical agent, such as a vulnerary agent, a peptic ulcer-treating agent, a carcinostatic or an agent for artificial skin, it has not been put to practical use. The characteristic action and effect of the EGF is that is proliferates fibloblasts as well as epitheliocytes, and for this effect, it is suitable for the treatment of injury which has reached connective tissues, but it is hardly most suited for the treatment of injury and dermoulcer where only epidermis is the lesion. In view of canceration inducing action, EGF should be cautiously put to practical use.

Also, FGF (fibloblast growth factor) which is being developed as a vulneary agent like EGF mainly accelerates growth of fibloblasts, and selective proliferation of epitheliocytes only is unattainable. Although TGF-α which is structurally analogous to EGF also possesses epitheliocyte growth accelerating activity, administration thereof to humans or animals is considered to be difficult due to a grave defect that it also possesses cancerating activity as the name, transforming growth factor, i.e. canceration accelerating factor, indicates.

SUMMARY OF THE INVENTION

The object of the present invention is to provide a heretofore unknown pharmaceutical agent which specifically accelerates growth of normal epitheliocytes only and does not have fibloblast growth accelerating action or cancerating action.

Selective proliferation of normal epitheliocytes only is extremely useful for the treatment of injury dermoulcer in the surface layer, which have not reaches connective tissues. For example, the patients who underwent examination of bedsores, which has been becoming a serious problem as the bedridden old people increase, number to 65000, and the potential patients having bedsore are estimated to be 10 times said number. This is a symptom induced by a decrease of the regeneration speed of epitheliocytes because of old age. If new epitheliocytes can be formed quickly and regeneration can be enhanced before the condition becomes more serious and the lesion spreads into subcutaneous tissues, efficacious treatment and prevention will become possible.

Even when an injury which has reached the connective tissues is the treatment target, a protection will be given to the lesion if epithelial tissues can cover the lesion quickly, and autonomous regeneration of the skin tissues will proceed promptly. On the contrary, however, excessive growth of fibloblasts during the recovery of an injury leads to incomplete new formation of epitheliocytes, i.e. cicatrix. In every surgery, post-operative skin suture is important for phylaxis, and quick adhesion of epithelial tissues and less scars left on the skin surface after healing will be greatly advantageous.

A pharmaceutical agent which selectively proliferates only epitheliocytes is effective for healing of an injury irrespective of the agent being used solely or in combination with other agent which also accelerates growth of fibloblasts, such as EGP.

An agent which selectively proliferates only normal epitheliocytes is considered to be more specific and exerts higher effects than EGF in various application ranges conventionally considered to be the effective ranges of EGF, such as corneal operation, peptic ulcer and artificial skin. In addition, acceleration of epithelium regeneration is expected to result in improved metabolism of the skin which is useful for keeping the skin young, exploiting a wide range of use as cosmetics.

As new uses, expected are hair restoration, post-operative skin recovery, metabolism acceleration of keratinized skin, and recovery of epidermis after sunburn or atopic dermatitis. In connection with the hair restoration, while pharmaceutical agents which activate hair root cells by way of promoting blood circulation are being marketed, more direct effect will be obtained if the growth of hair root cells can be accelerated by a pharmaceutical agent which selectively proliferates only normal epitheliocytes.

DETAILED DESCRIPTION OF THE INVENTION

Figure 1:
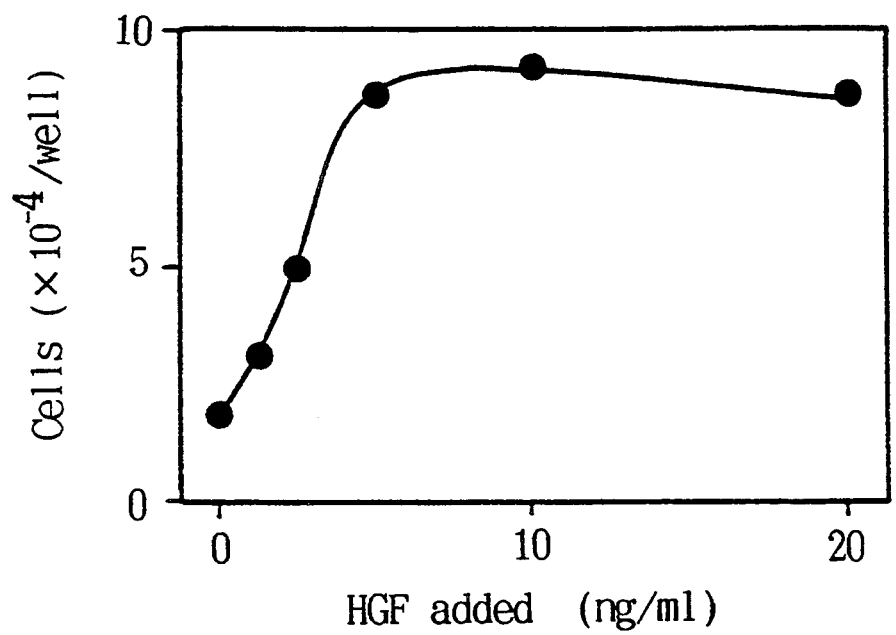
FIG. 1 shows the accelerating effect of HGF on the growth of human normal epidermis melanocytes, wherein ● is the number of cells upon termination of cultures at each HGF concentration (Example 3).

The present invention relates to an epitheliocyte growth accelerator containing a hepatocyte growth factor (HGF) as the active ingredient. In the present invention, HGF may be derived from human tissues, animal tissues, or blood components, or it may be produced by genetic engineering. In this regard, the host cell to be used in the genetic engineering may be selected from among Escherichia coli, Bacillus subtilis, yeasts, filamentous fungi, plant cells and animal cells.

The hepatocyte growth factor (HGF) which is the active ingredient in the present invention is a protein found by the inventors of the present invention from serum of rat regenerating liver as a factor which proliferates mature hepatocytes in vitro [Biochem. Biophys. Res. Commun., 122, 1450 (1984)]. The inventors further succeeded in isolating an HGF from rat platelets [FFBS Letter, 22, 311 (1987)], and identified its amino acid sequence. Then, the inventors conducted cDNA cloning of human- and rat-originated HGFs based on the identified HGF amino acid sequence, and inserted the cDNAs in vectors and transformed animal cells with the expression vectors thus obtained, to give hepatocyte growth factors as proteins [human HGF: Nature, 342, 440 (1989), rat HGF: Procs. Natl. Acad. Sci., 87, 3200 (1900)].

The inventors of the present invention have studied a hepatocyte growth factor for many years, and as a result, have succeeded in isolating and purifying HGF. In the course of intensive studies of structural and activity examinations of HGF, they found presence of an activity which specifically accelerates growth of epithelicoytes—melanocytes and keratinocytes, which resulted in the completion of the present invention.

Besides markedly accelerating the growth of human normal epidermis keratinocytes and melanocytes at concentrations as low as 5–10 ng/ml, HGF was confirmed to possess an activity in improve motility of both cells, as demonstrated in the following Examples. What is material in regenerating tissues, such as in healing an injury is proliferation of the cells constituting the tissues, and accompanied movement of the proliferated cells to the injured sites, and the pharmaceutical agent of the present invention possesses both actions. While HGF is a polypeptide originally found as a hepatocyte growth accelerator, it has been found to be more practical for the reasons that it accelerates growth of epitheliocytes only and does not accelerate growth of mesenchymal cells, it does not have cancerating activity, and that it shows extremely high specificity as compared with EGF.

The HGF to be used in the present invention is a biologically active polypeptide which was found as a factor capable of growing mature rate hepatocytes in vitro, and has a molecular weight of 82–85 kD by SDS-polyacrylamide gel electrophoresis. Rat HGF has a heterodimer structure wherein α-chain of 463 amino acid residues and β-chain of 233 amino acid residues are crosslinked by one disulfide bond, both α- and β-chains having two glucosamine sugar chain binding sites. Human HGF has the same biological activity, and consists of α-chain of 463 amino acid residues and β-chain of 234 amino acid residues. In the α-chain, there are four kringle structures, and the amino acid sequence of the β-chain has about 37% homology with β-chain of plasmin having a serin protease activity. The amino acid sequence of human HGF precurosor and the base sequence of the gone encoding said amino acid sequence are shown in Sequence Listings 1 and 2.

Human HGF is biosynthesized as a precursor consisting of 728 amino acids as shown in Sequence Listing 2, which comprises α-chain of 463 amino acid residues (from the 32nd Gln to the 494th Arg in Sequence Listing 2), and β-chain of 234 amino acid residues (from the 495th Val to the 728th Ser in Sequence Listing 2).

The homology between the amino acid sequences of rat HGF and human HGF is extremely high and is 91.6% in α-chain and 88.9% in β-chain, and their activities have non-species specificity.

The HGF of the present invention can be obtained by various methods. For example, it can be obtained from organs such as liver, spleen, lung, bone marrow, brain, and placenta of mammals such as rat, cow, etc., human blood cells such as platelets and leukocytes, plasma, and serum by extraction and purification. It is also possible to obtain an HGF by cultivation of primary culture cells and strain cells capable of producing HGF, followed by separation and purification of the culture. Or a recombinant HGF can be obtained by a known genetic engineering comprising isolation of an HGF gene and transformation of a suitable host cell such as Escherichia coli, Bacillus subtilis, yeasts, filamentous fungi, plant cells and animal cells to give a culture of transformants, from which the objective recombinant hepatocyte growth factor can be obtained (Nature, 342, 440, 1989).

The thus-obtained HGF can be used in the present invention as long as it has a growth accelerating activity for epitheliocytes, even if the amino acid sequence is partially deleted and/or substituted, or other amino acid sequence is partially inserted, or sugars are similarly deleted and/or substituted. That is, the HGF in the present invention encompasses all HGFs as referred to in the above.

The HGF which is the active ingredient of the present invention has an excellent accelerating action on the growth of epitheliocytes, irrespective of from which of the mammals such as human, cow, horse, rat, sheep, etc. it is derived, and shows effective epitheliocyte growth accelerating activity for all mammals. That is, the epitheliocyte growth accelerator of the present invention can be used as a pharmaceutical for not only humans but also for animals.

The epitheliocyte growth accelerator of the present invention is preferably formulated into external medicines of cosmetics with an HGF, the active ingredient, solely, or in combination with other epitheliocyte growth accelerator and known carries. The epitheliocyte growth accelerator of the present invention may contain additives necessary for formulation, such as stabilizers, excipients, dissolution-promoters and antioxidants, besides an HGF. The additives are subject to no limitation as long as they are pharmacologically accepted. The epitheliocyte growth accelerator of the present invention can be formulated into various preparation forms such as ointment, gel, liquid, etc. according to the objective use. It is also possible to store the pharmaceutical agent of the present invention upon liophilization together with carries, and to prepare same into a liquid preparation when necessary.

The epitheliocyte growth accelerator of the present invention specifically accelerates growth of normal epitheliocytes, and improves cell motility. Therefore, it is pharmaceutically useful for the treatments of injury, dermoulcer and peptic ulcer. Also it is useful as a carcinostatic, an agent for post-operative skin suture and corneal operation, a growth agent for hair root cells, and an agent to be contained in cosmetics to enhance metabolism of the skin. Thus, the epitheliocyte growth accelerator of the present invention is useful not only as a therapeutic agent but also as a preventive.

Since HGF does not have fibloblast growing activity or canceration accelerating activity, as different from EGF, TFG-α and FGF, the accelerator of the present invention is highly useful as a heretofore unknown pharmaceutical having excellent specificity and less sideeffects.

The epitheliocyte growth accelerator of the present invention is administered via suitable administration routes according to the form of preparation, such as ointment. cataplasm, lotion, etc. by applying directly on the lesion, spraying an aqueous solution containing same, or the like. For example, when administering to a patient with bedsore of about a 10×10 cm² lesion. The dose ranges from 0.01 mg to 10 mg by the amount of HGF, which can be administered singly or in several times divided doses a day.

The present invention is hereinbelow described in detail by illustrating examples demonstrating embodiments and effects of the present invention, to which the present invention is not limited.

EXAMPLE 1

The hepatocyte growth factor (HGF) of the present invention was purified from a rat liver as in the following.

Carbon tetrachloride (0.2% body weight of rat) was intraperitoneally administered to a Wister rat, and 30 hours later, the lever was removed. The liver was homogenized by a whirling blender, after which it was centrifuged at 10,000 rpm for 20 minutes with a Hitachi 20 PR-52 cooling centrifuge to give a supernatant. The supernatant was dialyzed against 50 mM Tris hydrochloric acid buffer (pH 8.5) added with 0.15 M NaCl, 10 mM HEPES, 2 mM $CaCl_2$ and 0.01% Tween 80, at 4° C. for a whole day. The dialyzed solution was poured onto an S-Sepharose (FF, Pharmacia) column equilibrated with dialyzing buffer, and after washing, it was eluted with the gradient of NaCl. HGF was eluted at about 0.7 M NaCl concentration. This HGF was then purified by Blue Tris acryl M (IBF Corp.) chromatography. Elution was conducted with the gradient of arginine, and the HGF was eluted at about 0.25 M arginine concentration. The obtained fraction was then purified by Heparin-Sepharose (Pharmacia) chromatography. Elution was conducted with the gradient of NaCl, and the HGF was eluted at about 1 M NaCl concentration, which was then purified by Phenyl 5PW (Toso Corp.) chromatography. Elution was conducted with the decrease gradient of NaCl and the increase gradient of ethylene glycol, and thereby 10 μg of HGF was obtained from livers of 100 rats. Relative activity of the HGF was about 500,000 unit/mg. To the obtained HGF was added 0.25% BSA (bovine serum albumin) and the mixture was dialyzed against PBS (phosphate buffered saline).

EXAMPLE 2

Human cell-derived hepatocyte growth factor (HGF) was produced by genetic engineering.

In accordance with the Wigler method (Cell, 11, 223, 1977), mouse C127 cells transformed with a gene coding for the amino acid sequence of human hepatocyte growth factor were cultured, and a human hepatocyte growth factor was obtained from the culture supernatant thereof. That is, a cDNA library prepared from mRNA of human liver was subjected to screening, by which clone HAC19 and clone HBC25 coding for the amino acid sequence of the human hepatocyte growth factor were obtained.

DNAs from the HAC19 and the HBC25 were digested with BamHI and ScaI, and ScaI and PstI, respectively. The thus-obtained two DNA fragments were ligated with Blue Script KSII at BamHI and PstI sites to obtain pBS[hHGFII] (FERM BP-2990 deposited at the Fermentation Research Institute, Agency of Industrial Science and Technology, Ministry of International Trade and Industry, Japan). The pBS[hHGFII] was digested with XbaI, SalI and NaeI, and given blunt ends by T4 DNA polymerase, after which an about 2.3 Kb DNA fragment coding for the human hepatocyte growth factor was inserted at EcorRV site of an expression vector pBPMT constructed with bovine papilloma virus DNA as a vector, to give pBPMT[hHGFII]. The thus-obtained hepatocyte growth factor expression vector pBPMT[hHGFII] was used to transform mouse C127 cells by the calcium phosphate method. A transformant was selected according to growth in a medium containing G418. The cell line BPH89 which showed a high hepatocyte growth factor-producing activity was selected from among the transformants obtained. After the BPH89 cells were grown in a medium supplemented with fetal calf serum, the medium was changed every 2 days, followed by purification according to the purification method as described in Example 1.

A human HGF cDNA was also cloned from a human leukocyte cDNA library. A nucleotide and a deduced amino acid sequence are shown in Sequence Listings 1 and 2, respectively.

EXAMPLE 3

Effect on the growth of human normal epidermis melanocytes

The growth accelerating action of HGF which is the active ingredient of the epitheliocyte growth accelerator of the present invention, on melanocytes was confirmed in the following manner.

Human normal epidermis melanocytes (Kurabo) were suspended in a serum-free culture medium prepared by adding 5 μg/ml insulin, 0.5 μg/ml hydrocortisone, and 10 ng/ml phorhol-12-myristate-13-acetate (PMA) to MCDB 153 (high amino acid type) medium, and inoculated into a 12-well plastic plate at $10^4$ cells per well. After 24 hours' incubation at 37° C. in the presence of 10% $CO_2$, 25% $O_2$ and 65% $N_2$, the medium was changed to a test medium prepared by adding 0 to 20 ng/ml of HGF to a serum-free culture medium, and the incubation was continued. On the 9th day from the initiation of the incubation, the medium was changed to a test medium containing HGF, and 15 days later, the incubation was terminated. The cells were counted by a hemocytometer.

As a result, it was confirmed that the growth of normal melanocyte was accelerated dose-dependently by HGF in the range of 0–10 ng/ml, showing about 5 times enhanced growth at the optimum concentration, as can be seen in FIG. 1.

EXAMPLE 4

Effect on the Synthesis of Replication DNA by Human Normal Epidermis Melanocytes Human normal epidermis melanocytes were suspended in a serum-free culture medium as described in Example 3, and the cells were inoculated into a 24-well plastic plate at $4 \times 10^4$ cells/well. After 24 hours' incubation at 37° C. in the presence of 10% $CO_2$, 25% $O_2$ and 675% $N_2$, the medium was changed to a test medium prepared by adding 0 to 20 ng/ml of HGF to a serum-free culture medium, and the incubation was continued. After incubation for 24 hours, 0.5 μCl/ml of [$^{125}$I]deoxyuridine was added to each well. After the [$^{125}$I]deoxyuridine was taken into the cells by 4 hours' incubation, the cells were washed with PBS (phosphate buffered saline, pH 7.4), and precpitated with a cool aqueous solution of 10% trichloroacetate. The cells were subjected to lysis with 1 N sodium hydroxide solution, and radioactivity was measured by a gamma counter. Also, the sample which underwent radioactivity measurement was partially taken, and measured for protein amount by Micro BCA Protein Assay System (Pierce). The amount of the labeled deoxyuridine which had been taken into cells was estimated by subtracting the cell count of control, and converting into per 1 mg human normal epidermis melanocyte protein, which was taken as DNA synthesis activity (dpm/mg protein).

Figure 2:
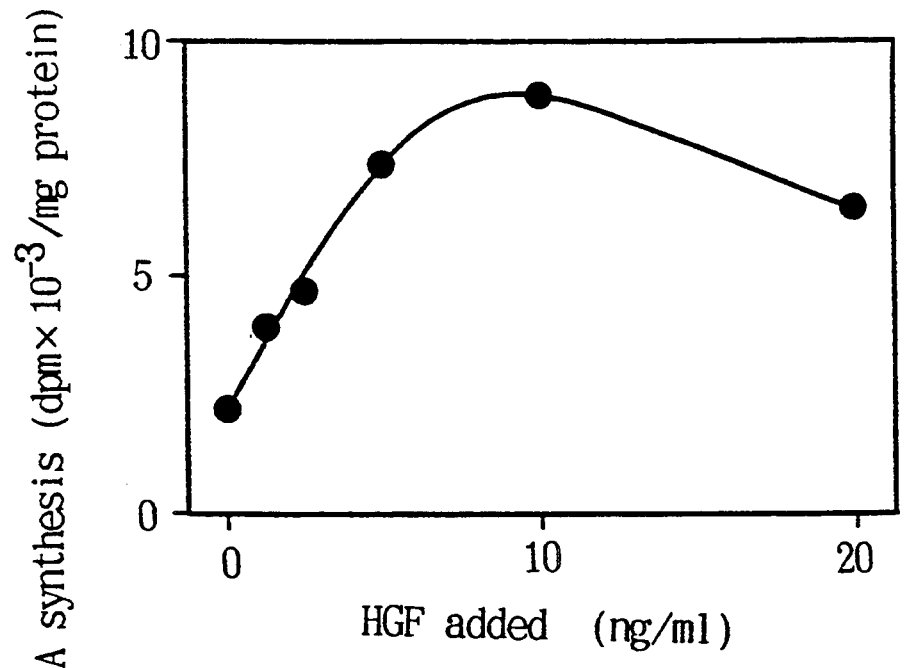
FIG. 2 shows the accelerating effect of HGF on the growth of human normal epidermis melanocytes, wherein ● is an amount of synthesized DNA per protein amount upon termination of culture at each HGF concentration (Example 4).

As a result, it was confirmed that the synthesis of replication DNA by normal epidermis melanocytes was accelerated dose-dependently by HGF in the range of 0–10 ng/ml, exhibiting about 4 times enhanced synthesis at the optimum concentration, as shown in FIG. 2.

EXAMPLE 5

Effect on the growth of human normal epidermis keratinocytes

The growth accelerating action of HGF which is the active ingredient of the epitheliocyte growth accelerator of the present invention, on keratinocytes was confirmed in the following manner.

Human normal epidermis keratinocytes were suspended in a medium prepared by adding bovine hypothalamus extract (150 μg protein/ml) to a serum-free culture medium as described in Example 3, and seeded into a 12-well plastic plate at $10^4$ cells/well. After 24 hours' incubation at 37° C. in the presence of 10% $CO_2$, 25% $O_2$ and 65% $N_2$, the medium was changed to a serum-free culture medium having a calcium ion concentration adjusted to 1.8 mM, followed by 24 hours' incubation. HGF was added thereto from 0 to 20 ng/ml, and the incubation was continued. On the 6th day from the initiation of the incubation, the medium was changed to a new medium containing HGF, and 4 days later (10th day from the initiation of the incubation), the incubation was terminated. The cells were counted by a hemocytometer.

Figure 3:
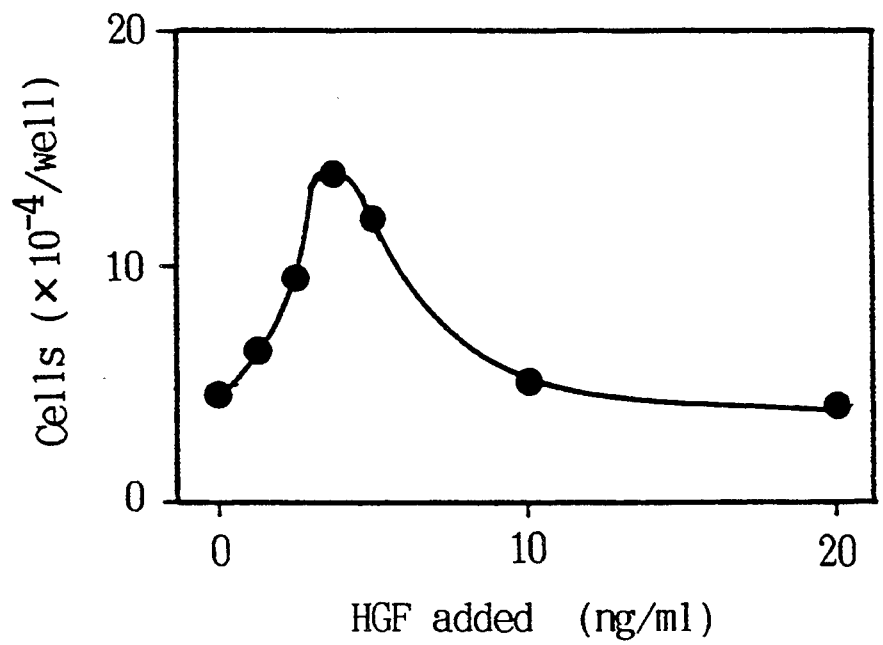
FIG. 3 shows the accelerating effect of HGF on the growth of human normal epidermis keratinocytes, wherein ● is the number of cells upon termination of culture at each HGF concentration (Example 5).

As a result, it was confirmed that the growth of normal keratinocytes was accelerated dose-dependently by HGF in the range of 0–2.5 ng/ml, exhibiting about 3 times enhanced growth at the optimum concentration, as shown in FIG. 3.

EXAMPLE 6

Effect on the Synthesis of Replication DNA by Human Normal Epidermis Keratinocytes Human normal epidermis keratinocytes were suspended in a medium prepared by adding bovine hypothalamus extract (150 μg protein/ml) to a serum-free culture medium as described in Example 3, and seeded into a 24-well plastic plate at $4 \times 10^4$ cells/well. After 24 hours' incubation at 37° C. in the presence of 10% $CO_2$, 25% $O_2$ and 65% $N_2$, the medium was changed to a serum-free culture medium having a calcium ion concentration adjusted to 1.8 mM, followed by 24 hours' incubation. HGF was added thereto from 0 to 20 ng/ml, and the incubation was continued. After 24 hours of incubation, 0.5 μCl/ml of [$^{125}$I]deoxyuridine was added to each well. After the [$^{125}$I]deoxyuridine was taken into the cells by 4 hours' incubation, the cells were washed twice with PBS (phosphate buffered saline, pH 7.4), and precipitated with a cool aqueous solution of 10% trichloroacetate. The cells were subjected to lysis with 1 N sodium hydroxide solution and radioactivity was measured by a gamma counter. Also, the sample which underwent radioactivity measurement was partially taken, and measured for protein amount by Micro BCA Protein Assay System (Pierce). The amount of the labeled deoxyuridine which had been taken into the cells was estimated by subtracting the cell count of control, and converting into per 1 mg human normal epidermis keratinocyte protein, which was taken as DNA synthesis activity (dpm/mg protein).

Figure 4:
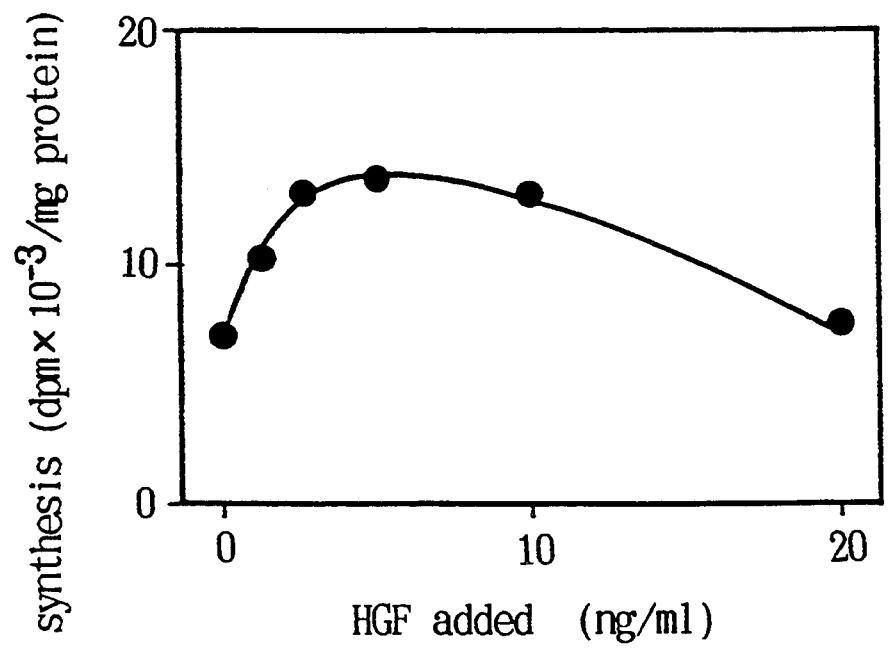
FIG. 4 shows the accelerating effect of HGF on the growth of human normal epidermis keratinocytes, wherein ● is an amount of synthesized DNA per protein amount upon termination of culture at each HGF concentration (Example 6).

As a result, it was confirmed that the synthesis of replication DNA by normal epidermis keratinocytes was accelerated dose-dependently by HGF in the range of 0–5 ng/ml, exhibiting about 2 times enhanced synthesis at the optimum concentration, as shown in FIG. 4.

EXAMPLE 7

Effect on the growth of Human Normal Epidermis Keratinocytes

Human normal epidermis keratinocytes were suspended in a medium prepared by adding bovine hypothalamus extract (150 µg protein/ml) to a serum-free culture medium as described in Example 3, and seeded into a 12-well plastic plate at $2 \times 10^4$ cells/well. After two days' incubation at 37° C. in the presence of 10% $CO_2$, 25% $O_2$ and 65%, $N_2$, the medium was changed to a serum-free culture medium having a calcium ion concentration adjusted to 1.8 mM, followed by two days' incubation. HGF (2.5 ng/ml) was added thereto, and the incubation was continued. Twenty-four hours later (5th day from the initiation of the incubation), the growth of the cells was observed with a microscope.

Figure 5A:
FIGS. 5a, and b are microscope photographs showing the accelerating effect of HGF on the growth of human normal epidermis keratinocytes, wherein (a) is a culture without HGF, and (b) is a culture added with 2.5 ng/ml HGF (Example 7).
Figure 5B:
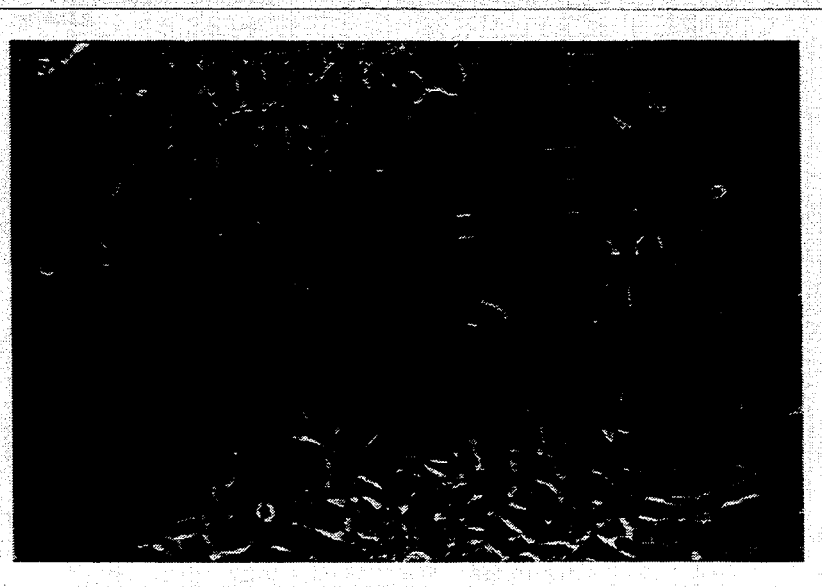

As a result, normal keratinocytes incubated in a culture medium containing HGF showed the growth apparently accelerated by HGF as compared with that without HGF, as shown in FIG. 5.

EXAMPLE 8

Effect on the Cell Motility of Human Normal Epidermis Keratinocytes

The cell motility improving action of HGF which is the active ingredient of the epitheliocyte growth accelerator of the present invention, on keratinocytes was confirmed in the following manner.

Human normal epidermis keratinocytes were suspended in a medium prepared by adding bovine hypothalamus extract (150 µg protein/ml) to a serum-free culture medium as described in Example 3, and seeded into a 12-well plastic plate at $2 \times 10^4$ cells/well. After two days' incubation at 37° C. in the presence of 10% $CO_2$, 25% $O_2$ and 65% $N_2$, the medium was changed to a serum-free culture medium supplemented with no bovine hypothalamus extract, followed by 24 hours' incubation. HGF was added thereto from 0 to 10 ng/ml, and the incubation was continued. Twenty-four hours later (4th day from the initiation of the incubation), the incubation was terminated, and the state of the cells was observed with a microscope.

Figure 6D:
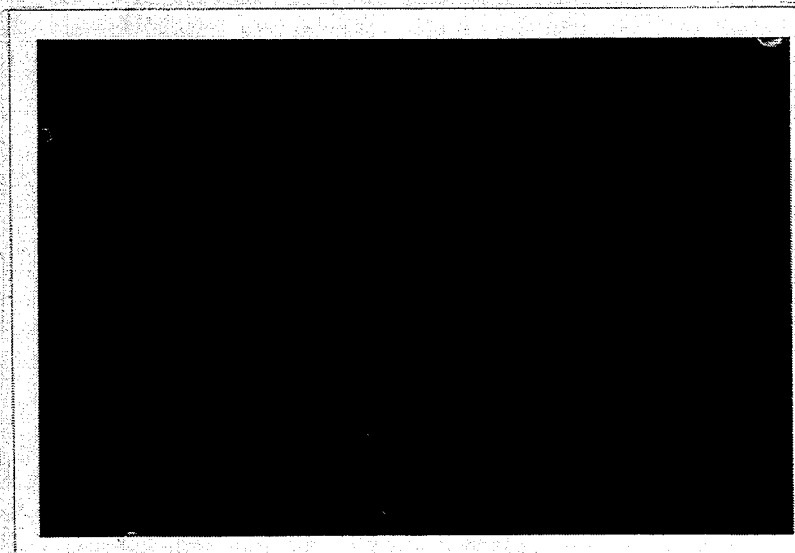
FIGS. 6a, b and c are microscope photographs showing the accelerating effect of HGF on the cell motility of human normal epidermis keratinocytes, wherein (a) is a culture without HGF, (b) is a culture added with 1 ng/ml HGF, and (c) is a culture added with 10 ng/ml HGF (Example 8).
Figure 6B:
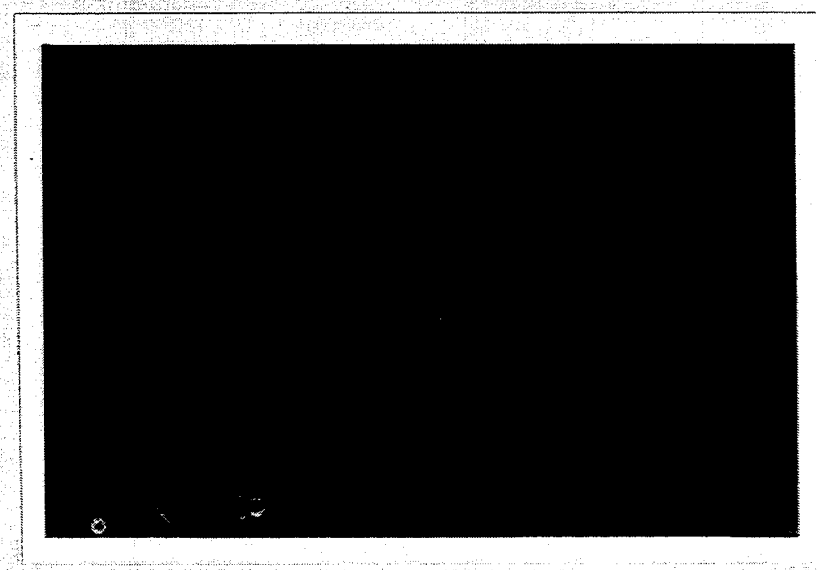
Figure 6C:
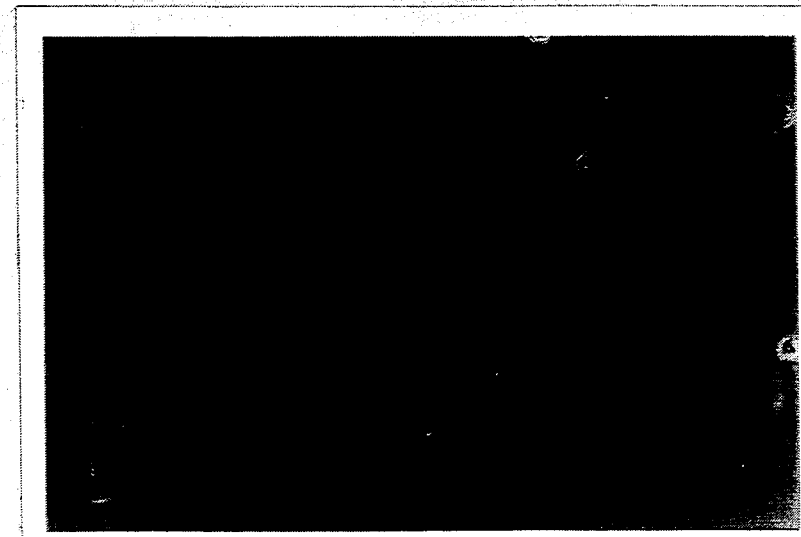

As a result, it was confirmed that human normal keratinocytes incubated in a medium containing HGF had an increased motility as a result of weakened adhesion between the cells, as compared with when no HGF was added, as shown in FIG. 6.

EXPERIMENT EXAMPLE

Effect of EGF and TGF-α on Cell Motility of Human Normal Epidermis Keratinocytes The cell motility improving action of EGF and TGF-α which also proliferate epitheliocytes as does the HGF or the active ingredient of the epitheliocyte growth accelerator of the present invention, on keratinocytes was confirmed in the same manner as in Example 8.

Human normal epidermis keratinocytes were suspended in a medium prepared by adding bovine hypothalamus extract (150 µg protein/ml) to a serum-free culture medium as described in Example 3, and seeded into a 12-well plastic plate at $2 \times 10^4$ cells/well. After two days' incubation at 37° C. in the presence of 10% $CO_2$, 25% $O_2$ and 65% $N_2$, the medium was changed to a serum-free culture medium supplemented with no bovine hypothalamus extract, followed by 24 hours' incubation. EGF or TGF-α was added thereto at 10 ng/ml, and the incubation was continued. Twenty-four hours later (4th day from the initiation of the incubation), the incubation was terminated, and the state of the cells was observed with a microscope.

Figure 7A:
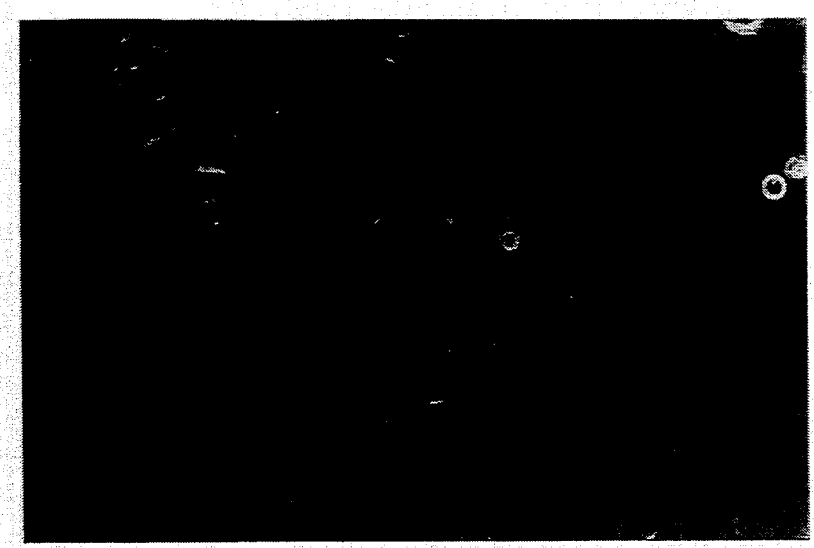
FIGS. 7a, and b are microscope photographs showing the accelerating effects of EGF and TGF-α on the cell motility of human normal epidermis keratinocytes, wherein (a) is a culture added with 10 ng/ml EGF, and (b) is a culture added with 10 ng/ml TGF-α (Experiment Example).
Figure 7B:

As is clear from the results shown in FIG. 7, human normal keratinocytes incubated in a medium containing EGF of TGF-α showed no change of adhesion between the cells, as compared with when added with HGF (FIG. 6), and the absence of improving effect on cell motility by EGF or TGF-α was confirmed.

FORMULATION EXAMPLE

HGF (10 mg) is mixed with hydrophilic petrolatum (250 g) by a conventional method to give an ointment.

---

What is claimed is:

1. A method for accelerating growth of epitheliocytes, which comprises administering an effective, accelerating amount of a native sequence mammalian hepatocyte growth factor (HGF) to a mammalian patient in need of such treatment.

2. A method according to claim 1, wherein the HGF is derived from human or animal tissues.

3. A method according to claim 1, wherein the HGF is produced by genetic engineering in a host cells.

4. A method according to claim 3, wherein the host cell for the genetic engineering is selected from the group consisting of *Escherichia coli*, *Bacillus subtilis*, yeasts, filamentous fungi, plant cells, and animal cells.

5. The method of claim 1 wherein said HGF is human.

6. The method of claim 1 wherein said HGF is from a non-human mammalian species.

7. The method of claim 1 wherein HGF is administered in admixture with a pharmacologically acceptable additive.

8. The method of claim 1 wherein said administration accelerates the growth of epitheliocytes for a patient who is suffering from a decrease in the regeneration speed of epitheliocytes.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2184 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2184

( x i ) SEQUENCE DESCRIPTION: SEQ ID NO:1:

```
ATG  TGG  GTG  ACC  AAA  CTC  CTG  CCA  GCC  CTG  CTG  CTG  CAG  CAT  GTC  CTC         48
Met  Trp  Val  Thr  Lys  Leu  Leu  Pro  Ala  Leu  Leu  Leu  Gln  His  Val  Leu
 1             5                        10                       15

CTG  CAT  CTC  CTC  CTG  CTC  CCC  ATC  GCC  ATC  CCC  TAT  GCA  GAG  GGA  CAA         96
```

|  |  |  |  |  |  |  |  |  |  |  |  |  |  |  |  |
|---|---|---|---|---|---|---|---|---|---|---|---|---|---|---|---|
| Leu | His | Leu | Leu | Leu | Leu | Pro | Ile | Ala | Ile | Pro | Tyr | Ala | Glu | Gly | Gln |
|  |  |  | 20 |  |  |  |  | 25 |  |  |  |  | 30 |  |  |

| AGG | AAA | AGA | AGA | AAT | ACA | ATT | CAT | GAA | TTC | AAA | AAA | TCA | GCA | AAG | ACT | 144 |
|---|---|---|---|---|---|---|---|---|---|---|---|---|---|---|---|---|
| Arg | Lys | Arg | Arg | Asn | Thr | Ile | His | Glu | Phe | Lys | Lys | Ser | Ala | Lys | Thr |  |
|  |  | 35 |  |  |  |  | 40 |  |  |  |  | 45 |  |  |  |  |

| ACC | CTA | ATC | AAA | ATA | GAT | CCA | GCA | CTG | AAG | ATA | AAA | ACC | AAA | AAA | GTG | 192 |
|---|---|---|---|---|---|---|---|---|---|---|---|---|---|---|---|---|
| Thr | Leu | Ile | Lys | Ile | Asp | Pro | Ala | Leu | Lys | Ile | Lys | Thr | Lys | Lys | Val |  |
|  |  | 50 |  |  |  |  | 55 |  |  |  |  | 60 |  |  |  |  |

| AAT | ACT | GCA | GAC | CAA | TGT | GCT | AAT | AGA | TGT | ACT | AGG | AAT | AAA | GGA | CTT | 240 |
|---|---|---|---|---|---|---|---|---|---|---|---|---|---|---|---|---|
| Asn | Thr | Ala | Asp | Gln | Cys | Ala | Asn | Arg | Cys | Thr | Arg | Asn | Lys | Gly | Leu |  |
| 65 |  |  |  |  | 70 |  |  |  |  | 75 |  |  |  |  | 80 |  |

| CCA | TTC | ACT | TGC | AAG | GCT | TTT | GTT | TTT | GAT | AAA | GCA | AGA | AAA | CAA | TGC | 288 |
|---|---|---|---|---|---|---|---|---|---|---|---|---|---|---|---|---|
| Pro | Phe | Thr | Cys | Lys | Ala | Phe | Val | Phe | Asp | Lys | Ala | Arg | Lys | Gln | Cys |  |
|  |  |  |  | 85 |  |  |  |  | 90 |  |  |  |  | 95 |  |  |

| CTC | TGG | TTC | CCC | TTC | AAT | AGC | ATG | TCA | AGT | GGA | GTG | AAA | AAA | GAA | TTT | 336 |
|---|---|---|---|---|---|---|---|---|---|---|---|---|---|---|---|---|
| Leu | Trp | Phe | Pro | Phe | Asn | Ser | Met | Ser | Ser | Gly | Val | Lys | Lys | Glu | Phe |  |
|  |  |  | 100 |  |  |  |  | 105 |  |  |  |  | 110 |  |  |  |

| GGC | CAT | GAA | TTT | GAC | CTC | TAT | GAA | AAC | AAA | GAC | TAC | ATT | AGA | AAC | TGC | 384 |
|---|---|---|---|---|---|---|---|---|---|---|---|---|---|---|---|---|
| Gly | His | Glu | Phe | Asp | Leu | Tyr | Glu | Asn | Lys | Asp | Tyr | Ile | Arg | Asn | Cys |  |
|  |  | 115 |  |  |  |  | 120 |  |  |  |  | 125 |  |  |  |  |

| ATC | ATT | GGT | AAA | GGA | CGC | AGC | TAC | AAG | GGA | ACA | GTA | TCT | ATC | ACT | AAG | 432 |
|---|---|---|---|---|---|---|---|---|---|---|---|---|---|---|---|---|
| Ile | Ile | Gly | Lys | Gly | Arg | Ser | Tyr | Lys | Gly | Thr | Val | Ser | Ile | Thr | Lys |  |
|  | 130 |  |  |  |  | 135 |  |  |  |  | 140 |  |  |  |  |  |

| AGT | GGC | ATC | AAA | TGT | CAG | CCC | TGG | AGT | TCC | ATG | ATA | CCA | CAC | GAA | CAC | 480 |
|---|---|---|---|---|---|---|---|---|---|---|---|---|---|---|---|---|
| Ser | Gly | Ile | Lys | Cys | Gln | Pro | Trp | Ser | Ser | Met | Ile | Pro | His | Glu | His |  |
| 145 |  |  |  |  | 150 |  |  |  |  | 155 |  |  |  |  | 160 |  |

| AGC | TTT | TTG | CCT | TCG | AGC | TAT | CGG | GGT | AAA | GAC | CTA | CAG | GAA | AAC | TAC | 528 |
|---|---|---|---|---|---|---|---|---|---|---|---|---|---|---|---|---|
| Ser | Phe | Leu | Pro | Ser | Ser | Tyr | Arg | Gly | Lys | Asp | Leu | Gln | Glu | Asn | Tyr |  |
|  |  |  |  | 165 |  |  |  |  | 170 |  |  |  |  | 175 |  |  |

| TGT | CGA | AAT | CCT | CGA | GGG | GAA | GAA | GGG | GGA | CCC | TGG | TGT | TTC | ACA | AGC | 576 |
|---|---|---|---|---|---|---|---|---|---|---|---|---|---|---|---|---|
| Cys | Arg | Asn | Pro | Arg | Gly | Glu | Glu | Gly | Gly | Pro | Trp | Cys | Phe | Thr | Ser |  |
|  |  |  | 180 |  |  |  |  | 185 |  |  |  |  | 190 |  |  |  |

| AAT | CCA | GAG | GTA | CGC | TAC | GAA | GTC | TGT | GAC | ATT | CCT | CAG | TGT | TCA | GAA | 624 |
|---|---|---|---|---|---|---|---|---|---|---|---|---|---|---|---|---|
| Asn | Pro | Glu | Val | Arg | Tyr | Glu | Val | Cys | Asp | Ile | Pro | Gln | Cys | Ser | Glu |  |
|  |  | 195 |  |  |  |  | 200 |  |  |  |  | 205 |  |  |  |  |

| GTT | GAA | TGC | ATG | ACC | TGC | AAT | GGG | GAG | AGT | TAT | CGA | GGT | CTC | ATG | GAT | 672 |
|---|---|---|---|---|---|---|---|---|---|---|---|---|---|---|---|---|
| Val | Glu | Cys | Met | Thr | Cys | Asn | Gly | Glu | Ser | Tyr | Arg | Gly | Leu | Met | Asp |  |
|  | 210 |  |  |  |  | 215 |  |  |  |  | 220 |  |  |  |  |  |

| CAT | ACA | GAA | TCA | GGC | AAG | ATT | TGT | CAG | CGC | TGG | GAT | CAT | CAG | ACA | CCA | 720 |
|---|---|---|---|---|---|---|---|---|---|---|---|---|---|---|---|---|
| His | Thr | Glu | Ser | Gly | Lys | Ile | Cys | Gln | Arg | Trp | Asp | His | Gln | Thr | Pro |  |
| 225 |  |  |  |  | 230 |  |  |  |  | 235 |  |  |  |  | 240 |  |

| CAC | CGG | CAC | AAA | TTC | TTG | CCT | GAA | AGA | TAT | CCC | GAC | AAG | GGC | TTT | GAT | 768 |
|---|---|---|---|---|---|---|---|---|---|---|---|---|---|---|---|---|
| His | Arg | His | Lys | Phe | Leu | Pro | Glu | Arg | Tyr | Pro | Asp | Lys | Gly | Phe | Asp |  |
|  |  |  |  | 245 |  |  |  |  | 250 |  |  |  |  | 255 |  |  |

| GAT | AAT | TAT | TGC | CGC | AAT | CCC | GAT | GGC | CAG | CCG | AGG | CCA | TGG | TGC | TAT | 816 |
|---|---|---|---|---|---|---|---|---|---|---|---|---|---|---|---|---|
| Asp | Asn | Tyr | Cys | Arg | Asn | Pro | Asp | Gly | Gln | Pro | Arg | Pro | Trp | Cys | Tyr |  |
|  |  |  | 260 |  |  |  |  | 265 |  |  |  |  | 270 |  |  |  |

| ACT | CTT | GAC | CCT | CAC | ACC | CGC | TGG | GAG | TAC | TGT | GCA | ATT | AAA | ACA | TGC | 864 |
|---|---|---|---|---|---|---|---|---|---|---|---|---|---|---|---|---|
| Thr | Leu | Asp | Pro | His | Thr | Arg | Trp | Glu | Tyr | Cys | Ala | Ile | Lys | Thr | Cys |  |
|  |  | 275 |  |  |  |  | 280 |  |  |  |  | 285 |  |  |  |  |

| GCT | GAC | AAT | ACT | ATG | AAT | GAC | ACT | GAT | GTT | CCT | TTG | GAA | ACA | ACT | GAA | 912 |
|---|---|---|---|---|---|---|---|---|---|---|---|---|---|---|---|---|
| Ala | Asp | Asn | Thr | Met | Asn | Asp | Thr | Asp | Val | Pro | Leu | Glu | Thr | Thr | Glu |  |
|  | 290 |  |  |  |  | 295 |  |  |  |  | 300 |  |  |  |  |  |

| TGC | ATC | CAA | GGT | CAA | GGA | GAA | GGC | TAC | AGG | GGC | ACT | GTC | AAT | ACC | ATT | 960 |
|---|---|---|---|---|---|---|---|---|---|---|---|---|---|---|---|---|
| Cys | Ile | Gln | Gly | Gln | Gly | Glu | Gly | Tyr | Arg | Gly | Thr | Val | Asn | Thr | Ile |  |
| 305 |  |  |  |  | 310 |  |  |  |  | 315 |  |  |  |  | 320 |  |

| TGG | AAT | GGA | ATT | CCA | TGT | CAG | CGT | TGG | GAT | TCT | CAG | TAT | CCT | CAC | GAG | 1008 |
|---|---|---|---|---|---|---|---|---|---|---|---|---|---|---|---|---|
| Trp | Asn | Gly | Ile | Pro | Cys | Gln | Arg | Trp | Asp | Ser | Gln | Tyr | Pro | His | Glu |  |
|  |  |  |  | 325 |  |  |  |  | 330 |  |  |  |  | 335 |  |  |

| CAT | GAC | ATG | ACT | CCT | GAA | AAT | TTC | AAG | TGC | AAG | GAC | CTA | CGA | GAA | AAT | 1056 |
|---|---|---|---|---|---|---|---|---|---|---|---|---|---|---|---|---|
| His | Asp | Met | Thr | Pro | Glu | Asn | Phe | Lys | Cys | Lys | Asp | Leu | Arg | Glu | Asn |  |
|  |  |  | 340 |  |  |  |  | 345 |  |  |  |  | 350 |  |  |  |

-continued

| | | | | | | | | | | | | | | | | |
|---|---|---|---|---|---|---|---|---|---|---|---|---|---|---|---|---|
| TAC | TGC | CGA | AAT | CCA | GAT | GGG | TCT | GAA | TCA | CCC | TGG | TGT | TTT | ACC | ACT | 1104 |
| Tyr | Cys | Arg | Asn | Pro | Asp | Gly | Ser | Glu | Ser | Pro | Trp | Cys | Phe | Thr | Thr | |
| | | 355 | | | | | 360 | | | | | 365 | | | | |
| GAT | CCA | AAC | ATC | CGA | GTT | GGC | TAC | TGC | TCC | CAA | ATT | CCA | AAC | TGT | GAT | 1152 |
| Asp | Pro | Asn | Ile | Arg | Val | Gly | Tyr | Cys | Ser | Gln | Ile | Pro | Asn | Cys | Asp | |
| | 370 | | | | | 375 | | | | | 380 | | | | | |
| ATG | TCA | CAT | GGA | CAA | GAT | TGT | TAT | CGT | GGG | AAT | GGC | AAA | AAT | TAT | ATG | 1200 |
| Met | Ser | His | Gly | Gln | Asp | Cys | Tyr | Arg | Gly | Asn | Gly | Lys | Asn | Tyr | Met | |
| 385 | | | | | 390 | | | | | 395 | | | | | 400 | |
| GGC | AAC | TTA | TCC | CAA | ACA | AGA | TCT | GGA | CTA | ACA | TGT | TCA | ATG | TGG | GAC | 1248 |
| Gly | Asn | Leu | Ser | Gln | Thr | Arg | Ser | Gly | Leu | Thr | Cys | Ser | Met | Trp | Asp | |
| | | | | 405 | | | | | 410 | | | | | 415 | | |
| AAG | AAC | ATG | GAA | GAC | TTA | CAT | CGT | CAT | ATC | TTC | TGG | GAA | CCA | GAT | GCA | 1296 |
| Lys | Asn | Met | Glu | Asp | Leu | His | Arg | His | Ile | Phe | Trp | Glu | Pro | Asp | Ala | |
| | | | 420 | | | | | 425 | | | | | 430 | | | |
| AGT | AAG | CTG | AAT | GAG | AAT | TAC | TGC | CGA | AAT | CCA | GAT | GAT | GAT | GCT | CAT | 1344 |
| Ser | Lys | Leu | Asn | Glu | Asn | Tyr | Cys | Arg | Asn | Pro | Asp | Asp | Asp | Ala | His | |
| | | 435 | | | | | 440 | | | | | 445 | | | | |
| GGA | CCC | TGG | TGC | TAC | ACG | GGA | AAT | CCA | CTC | ATT | CCT | TGG | GAT | TAT | TGC | 1392 |
| Gly | Pro | Trp | Cys | Tyr | Thr | Gly | Asn | Pro | Leu | Ile | Pro | Trp | Asp | Tyr | Cys | |
| | 450 | | | | | 455 | | | | | 460 | | | | | |
| CCT | ATT | TCT | CGT | TGT | GAA | GGT | GAT | ACC | ACA | CCT | ACA | ATA | GTC | AAT | TTA | 1440 |
| Pro | Ile | Ser | Arg | Cys | Glu | Gly | Asp | Thr | Thr | Pro | Thr | Ile | Val | Asn | Leu | |
| 465 | | | | | 470 | | | | | 475 | | | | | 480 | |
| GAC | CAT | CCC | GTA | ATA | TCT | TGT | GCC | AAA | ACG | AAA | CAA | TTG | CGA | GTT | GTA | 1488 |
| Asp | His | Pro | Val | Ile | Ser | Cys | Ala | Lys | Thr | Lys | Gln | Leu | Arg | Val | Val | |
| | | | | 485 | | | | | 490 | | | | | 495 | | |
| AAT | GGG | ATT | CCA | ACA | CGA | ACA | AAC | ATA | GGA | TGG | ATG | GTT | AGT | TTG | AGA | 1536 |
| Asn | Gly | Ile | Pro | Thr | Arg | Thr | Asn | Ile | Gly | Trp | Met | Val | Ser | Leu | Arg | |
| | | | 500 | | | | | 505 | | | | | 510 | | | |
| TAC | AGA | AAT | AAA | CAT | ATC | TGC | GGA | GGA | TCA | TTG | ATA | AAG | GAG | AGT | TGG | 1584 |
| Tyr | Arg | Asn | Lys | His | Ile | Cys | Gly | Gly | Ser | Leu | Ile | Lys | Glu | Ser | Trp | |
| | | | 515 | | | | 520 | | | | | 525 | | | | |
| GTT | CTT | ACT | GCA | CGA | CAG | TGT | TTC | CCT | TCT | CGA | GAC | TTG | AAA | GAT | TAT | 1632 |
| Val | Leu | Thr | Ala | Arg | Gln | Cys | Phe | Pro | Ser | Arg | Asp | Leu | Lys | Asp | Tyr | |
| | | 530 | | | | | 535 | | | | | 540 | | | | |
| GAA | GCT | TGG | CTT | GGA | ATT | CAT | GAT | GTC | CAC | GGA | AGA | GGA | GAT | GAG | AAA | 1680 |
| Glu | Ala | Trp | Leu | Gly | Ile | His | Asp | Val | His | Gly | Arg | Gly | Asp | Glu | Lys | |
| 545 | | | | | 550 | | | | | 555 | | | | | 560 | |
| TGC | AAA | CAG | GTT | CTC | AAT | GTT | TCC | CAG | CTG | GTA | TAT | GGC | CCT | GAA | GGA | 1728 |
| Cys | Lys | Gln | Val | Leu | Asn | Val | Ser | Gln | Leu | Val | Tyr | Gly | Pro | Glu | Gly | |
| | | | | 565 | | | | | 570 | | | | | 575 | | |
| TCA | GAT | CTG | GTT | TTA | ATG | AAG | CTT | GCC | AGG | CCT | GCT | GTC | CTG | GAT | GAT | 1776 |
| Ser | Asp | Leu | Val | Leu | Met | Lys | Leu | Ala | Arg | Pro | Ala | Val | Leu | Asp | Asp | |
| | | | 580 | | | | | 585 | | | | | 590 | | | |
| TTT | GTT | AGT | ACG | ATT | GAT | TTA | CCT | AAT | TAT | GGA | TGC | ACA | ATT | CCT | GAA | 1824 |
| Phe | Val | Ser | Thr | Ile | Asp | Leu | Pro | Asn | Tyr | Gly | Cys | Thr | Ile | Pro | Glu | |
| | | 595 | | | | | 600 | | | | | 605 | | | | |
| AAG | ACC | AGT | TGC | AGT | GTT | TAT | GGC | TGG | GGC | TAC | ACT | GGA | TTG | ATC | AAC | 1872 |
| Lys | Thr | Ser | Cys | Ser | Val | Tyr | Gly | Trp | Gly | Tyr | Thr | Gly | Leu | Ile | Asn | |
| | 610 | | | | | 615 | | | | | 620 | | | | | |
| TAT | GAT | GGC | CTA | TTA | CGA | GTG | GCA | CAT | CTC | TAT | ATA | ATG | GGA | AAT | GAG | 1920 |
| Tyr | Asp | Gly | Leu | Leu | Arg | Val | Ala | His | Leu | Tyr | Ile | Met | Gly | Asn | Glu | |
| 625 | | | | | 630 | | | | | 635 | | | | | 640 | |
| AAA | TGC | AGC | CAG | CAT | CAT | CGA | GGG | AAG | GTG | ACT | CTG | AAT | GAG | TCT | GAA | 1968 |
| Lys | Cys | Ser | Gln | His | His | Arg | Gly | Lys | Val | Thr | Leu | Asn | Glu | Ser | Glu | |
| | | | | 645 | | | | | 650 | | | | | 655 | | |
| ATA | TGT | GCT | GGG | GCT | GAA | AAG | ATT | GGA | TCA | GGA | CCA | TGT | GAG | GGG | GAT | 2016 |
| Ile | Cys | Ala | Gly | Ala | Glu | Lys | Ile | Gly | Ser | Gly | Pro | Cys | Glu | Gly | Asp | |
| | | | 660 | | | | | 665 | | | | | 670 | | | |
| TAT | GGT | GGC | CCA | CTT | GTT | TGT | GAG | CAA | CAT | AAA | ATG | AGA | ATG | GTT | CTT | 2064 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Tyr | Gly | Gly | Pro | Leu | Val | Cys | Glu | Gln | His | Lys | Met | Arg | Met | Val | Leu |      |
|     | 675 |     |     |     | 680 |     |     |     |     | 685 |     |     |     |     |     |      |
| GGT | GTC | ATT | GTT | CCT | GGT | CGT | GGA | TGT | GCC | ATT | CCA | AAT | CGT | CCT | GGT | 2112 |
| Gly | Val | Ile | Val | Pro | Gly | Arg | Gly | Cys | Ala | Ile | Pro | Asn | Arg | Pro | Gly |      |
|     | 690 |     |     |     |     | 695 |     |     |     |     | 700 |     |     |     |     |      |
| ATT | TTT | GTC | CGA | GTA | GCA | TAT | TAT | GCA | AAA | TGG | ATA | CAC | AAA | ATT | ATT | 2160 |
| Ile | Phe | Val | Arg | Val | Ala | Tyr | Tyr | Ala | Lys | Trp | Ile | His | Lys | Ile | Ile |      |
| 705 |     |     |     |     | 710 |     |     |     |     | 715 |     |     |     |     | 720 |      |
| TTA | ACA | TAT | AAG | GTA | CCA | CAG | TCA |     |     |     |     |     |     |     |     | 2184 |
| Leu | Thr | Tyr | Lys | Val | Pro | Gln | Ser |     |     |     |     |     |     |     |     |      |
|     |     |     |     | 725 |     |     |     |     |     |     |     |     |     |     |     |      |

( 2 ) INFORMATION FOR SEQ ID NO:2:

( i ) SEQUENCE CHARACTERISTICS:
        ( A ) LENGTH: 728 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Met | Trp | Val | Thr | Lys | Leu | Leu | Pro | Ala | Leu | Leu | Gln | His | Val | Leu |
| 1   |     |     |     | 5   |     |     |     |     | 10  |     |     |     | 15  |     |
| Leu | His | Leu | Leu | Leu | Leu | Pro | Ile | Ala | Ile | Pro | Tyr | Ala | Glu | Gly | Gln |
|     |     |     | 20  |     |     |     | 25  |     |     |     | 30  |     |     |     |     |
| Arg | Lys | Arg | Arg | Asn | Thr | Ile | His | Glu | Phe | Lys | Lys | Ser | Ala | Lys | Thr |
|     |     | 35  |     |     |     |     | 40  |     |     |     |     | 45  |     |     |     |
| Thr | Leu | Ile | Lys | Ile | Asp | Pro | Ala | Leu | Lys | Ile | Lys | Thr | Lys | Lys | Val |
|     | 50  |     |     |     |     | 55  |     |     |     |     | 60  |     |     |     |     |
| Asn | Thr | Ala | Asp | Gln | Cys | Ala | Asn | Arg | Cys | Thr | Arg | Asn | Lys | Gly | Leu |
| 65  |     |     |     |     | 70  |     |     |     |     | 75  |     |     |     |     | 80  |
| Pro | Phe | Thr | Cys | Lys | Ala | Phe | Val | Phe | Asp | Lys | Ala | Arg | Lys | Gln | Cys |
|     |     |     |     | 85  |     |     |     |     | 90  |     |     |     |     | 95  |     |
| Leu | Trp | Phe | Pro | Phe | Asn | Ser | Met | Ser | Ser | Gly | Val | Lys | Lys | Glu | Phe |
|     |     |     | 100 |     |     |     | 105 |     |     |     | 110 |     |     |     |     |
| Gly | His | Glu | Phe | Asp | Leu | Tyr | Glu | Asn | Lys | Asp | Tyr | Ile | Arg | Asn | Cys |
|     |     | 115 |     |     |     |     | 120 |     |     |     |     | 125 |     |     |     |
| Ile | Ile | Gly | Lys | Gly | Arg | Ser | Tyr | Lys | Gly | Thr | Val | Ser | Ile | Thr | Lys |
|     | 130 |     |     |     |     | 135 |     |     |     |     | 140 |     |     |     |     |
| Ser | Gly | Ile | Lys | Cys | Gln | Pro | Trp | Ser | Ser | Met | Ile | Pro | His | Glu | His |
| 145 |     |     |     |     | 150 |     |     |     |     | 155 |     |     |     |     | 160 |
| Ser | Phe | Leu | Pro | Ser | Ser | Tyr | Arg | Gly | Lys | Asp | Leu | Gln | Glu | Asn | Tyr |
|     |     |     |     | 165 |     |     |     |     | 170 |     |     |     |     | 175 |     |
| Cys | Arg | Asn | Pro | Arg | Gly | Glu | Glu | Gly | Gly | Pro | Trp | Cys | Phe | Thr | Ser |
|     |     |     | 180 |     |     |     | 185 |     |     |     | 190 |     |     |     |     |
| Asn | Pro | Glu | Val | Arg | Tyr | Glu | Val | Cys | Asp | Ile | Pro | Gln | Cys | Ser | Glu |
|     |     | 195 |     |     |     |     | 200 |     |     |     |     | 205 |     |     |     |
| Val | Glu | Cys | Met | Thr | Cys | Asn | Gly | Glu | Ser | Tyr | Arg | Gly | Leu | Met | Asp |
|     | 210 |     |     |     |     | 215 |     |     |     |     | 220 |     |     |     |     |
| His | Thr | Glu | Ser | Gly | Lys | Ile | Cys | Gln | Arg | Trp | Asp | His | Gln | Thr | Pro |
| 225 |     |     |     |     | 230 |     |     |     |     | 235 |     |     |     |     | 240 |
| His | Arg | His | Lys | Phe | Leu | Pro | Glu | Arg | Tyr | Pro | Asp | Lys | Gly | Phe | Asp |
|     |     |     |     | 245 |     |     |     |     | 250 |     |     |     |     | 255 |     |
| Asp | Asn | Tyr | Cys | Arg | Asn | Pro | Asp | Gly | Gln | Pro | Arg | Pro | Trp | Cys | Tyr |
|     |     |     | 260 |     |     |     | 265 |     |     |     | 270 |     |     |     |     |
| Thr | Leu | Asp | Pro | His | Thr | Arg | Trp | Glu | Tyr | Cys | Ala | Ile | Lys | Thr | Cys |
|     |     | 275 |     |     |     |     | 280 |     |     |     |     | 285 |     |     |     |
| Ala | Asp | Asn | Thr | Met | Asn | Asp | Thr | Asp | Val | Pro | Leu | Glu | Thr | Thr | Glu |

```
      290              295              300
Cys Ile Gln Gly Gln Gly Glu Gly Tyr Arg Gly Thr Val Asn Thr Ile
305              310              315              320
Trp Asn Gly Ile Pro Cys Gln Arg Trp Asp Ser Gln Tyr Pro His Glu
              325              330              335
His Asp Met Thr Pro Glu Asn Phe Lys Cys Lys Asp Leu Arg Glu Asn
          340              345              350
Tyr Cys Arg Asn Pro Asp Gly Ser Glu Ser Pro Trp Cys Phe Thr Thr
      355              360              365
Asp Pro Asn Ile Arg Val Gly Tyr Cys Ser Gln Ile Pro Asn Cys Asp
      370              375              380
Met Ser His Gly Gln Asp Cys Tyr Arg Gly Asn Gly Lys Asn Tyr Met
385              390              395              400
Gly Asn Leu Ser Gln Thr Arg Ser Gly Leu Thr Cys Ser Met Trp Asp
              405              410              415
Lys Asn Met Glu Asp Leu His Arg His Ile Phe Trp Glu Pro Asp Ala
          420              425              430
Ser Lys Leu Asn Glu Asn Tyr Cys Arg Asn Pro Asp Asp Ala His
      435              440              445
Gly Pro Trp Cys Tyr Thr Gly Asn Pro Leu Ile Pro Trp Asp Tyr Cys
    450              455              460
Pro Ile Ser Arg Cys Glu Gly Asp Thr Thr Pro Thr Ile Val Asn Leu
465              470              475              480
Asp His Pro Val Ile Ser Cys Ala Lys Thr Lys Gln Leu Arg Val Val
              485              490              495
Asn Gly Ile Pro Thr Arg Thr Asn Ile Gly Trp Met Val Ser Leu Arg
              500              505              510
Tyr Arg Asn Lys His Ile Cys Gly Gly Ser Leu Ile Lys Glu Ser Trp
      515              520              525
Val Leu Thr Ala Arg Gln Cys Phe Pro Ser Arg Asp Leu Lys Asp Tyr
    530              535              540
Glu Ala Trp Leu Gly Ile His Asp Val His Gly Arg Gly Asp Glu Lys
545              550              555              560
Cys Lys Gln Val Leu Asn Val Ser Gln Leu Val Tyr Gly Pro Glu Gly
              565              570              575
Ser Asp Leu Val Leu Met Lys Leu Ala Arg Pro Ala Val Leu Asp Asp
              580              585              590
Phe Val Ser Thr Ile Asp Leu Pro Asn Tyr Gly Cys Thr Ile Pro Glu
      595              600              605
Lys Thr Ser Cys Ser Val Tyr Gly Trp Gly Tyr Thr Gly Leu Ile Asn
    610              615              620
Tyr Asp Gly Leu Leu Arg Val Ala His Leu Tyr Ile Met Gly Asn Glu
625              630              635              640
Lys Cys Ser Gln His His Arg Gly Lys Val Thr Leu Asn Glu Ser Glu
              645              650              655
Ile Cys Ala Gly Ala Glu Lys Ile Gly Ser Gly Pro Cys Glu Gly Asp
              660              665              670
Tyr Gly Gly Pro Leu Val Cys Glu Gln His Lys Met Arg Met Val Leu
          675              680              685
Gly Val Ile Val Pro Gly Arg Gly Cys Ala Ile Pro Asn Arg Pro Gly
      690              695              700
Ile Phe Val Arg Val Ala Tyr Tyr Ala Lys Trp Ile His Lys Ile Ile
705              710              715              720
Leu Thr Tyr Lys Val Pro Gln Ser
              725
```